(12) United States Patent
Hayashi et al.

(10) Patent No.: US 9,823,181 B2
(45) Date of Patent: Nov. 21, 2017

(54) $CP_2MG$ CONCENTRATION MEASURING DEVICE

(71) Applicant: HORIBA STEC, CO., LTD., Kyoto (JP)

(72) Inventors: Daisuke Hayashi, Kyoto (JP); Yuhei Sakaguchi, Kyoto (JP); Masakazu Minami, Kyoto (JP); Atsuko Teraoka, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 0 days.

(21) Appl. No.: 15/240,235

(22) Filed: Aug. 18, 2016

(65) Prior Publication Data

US 2017/0052115 A1   Feb. 23, 2017

(30) Foreign Application Priority Data

Aug. 20, 2015   (JP) ................. 2015-162471

(51) Int. Cl.
| | | |
|---|---|---|
| *G01J 5/02* | (2006.01) | |
| *G01N 21/05* | (2006.01) | |
| *G01N 21/3504* | (2014.01) | |
| *G01N 21/03* | (2006.01) | |

(52) U.S. Cl.
CPC ......... *G01N 21/05* (2013.01); *G01N 21/3504* (2013.01); *G01N 2021/0389* (2013.01)

(58) Field of Classification Search
CPC .... G01N 21/3504; G01N 21/05; G01N 21/61; G01N 2021/3185
See application file for complete search history.

(56) References Cited

U.S. PATENT DOCUMENTS

| | | | | |
|---|---|---|---|---|
| 3,886,364 A | * | 5/1975 | Walker | ............... G01N 21/0317 250/343 |
| 2012/0162655 A1 | * | 6/2012 | Oida | .................. G01N 21/3504 356/437 |

FOREIGN PATENT DOCUMENTS

JP    2006-324532    11/2006

OTHER PUBLICATIONS

Horiba Stec, Co., Ltd., "Presentation of Comprehensive Supply System for Diverse Semiconductor Materials," distributed at SEMICON Japan 2014, Dec. 5, 2014.

* cited by examiner

*Primary Examiner* — Kenneth J Malkowski
(74) *Attorney, Agent, or Firm* — Greenblum & Bernstein, P.L.C.

(57) ABSTRACT

The present invention intends to provide a $Cp_2Mg$ concentration measuring device capable of accurately measuring the concentration of $Cp_2Mg$ to be supplied to a process chamber without being affected by spontaneous decomposition, and is adapted to measure light intensity in a predetermined wavelength band around 12.8 μm and on the basis of the light intensity, calculate the concentration of $Cp_2Mg$ in a material gas.

6 Claims, 5 Drawing Sheets

CP$_2$MG CONCENTRATION MEASURING DEVICE

TECHNICAL FIELD

The present invention relates to a Cp$_2$Mg concentration measuring device adapted to measure the concentration of Cp$_2$Mg used for, for example, an LED manufacturing process.

BACKGROUND ART

Cp$_2$Mg (cyclopentadienyl magnesium) is used as, for example, a doping material for an AlGaInP-based compound semiconductor used for LEDs. As an example of a doping process, a process of introducing Cp$_2$Mg into a process chamber together with carrier gas (e.g., hydrogen gas), and doping a semiconductor with magnesium produced by thermally decomposing Cp$_2$Mg can be cited.

When performing this process, it is necessary to control the supply concentration of Cp$_2$Mg. For this purpose, in the past, an acoustic type concentration measuring device such as an ultrasonic concentration meter, or an optical type concentration measuring device as disclosed in Patent Literature 1 has been used to measure the concentration of Cp$_2$Mg in a supply pipe. In particular, in recent years, for some reasons such as the miniaturization of LEDs, a device capable of accurately measuring the concentration of Cp$_2$Mg down to low concentrations has been required.

However, as a result of intensive examination made by the present inventor in consideration of such a requirement, it has been found that it is difficult for the conventional concentration measuring device to obtain sufficient measurement accuracy.

The reason for this is as follows.

It is said that Cp$_2$Mg is a very stable material at temperatures lower than the temperature (approximately 300° C. to 500° C.) of thermal decomposition in a process chamber.

In addition, in the past, it has been considered that the inside of a supply pipe to the process chamber is kept at a temperature of, e.g., 30° C. to 50° C., which is far lower than the thermal decomposition temperature, and therefore inside the supply pipe, Cp$_2$Mg is not decomposed but circulates in a stable state.

On the other hand, the present inventor has first found that the decomposition of Cp$_2$Mg, which has been considered to be stable at low temperatures, occurs in an amount enough to cause a problem in highly accurate concentration measurement in a low concentration range although the amount is small.

Such decomposition results in the presence of a decomposed organic substance (such as methane) and magnesium in a supply pipe in addition to Cp$_2$Mg in carrier gas (hydrogen).

As a result, the acoustic type concentration measuring device adapted to, on the assumption that only one material is present in carrier gas, measure the concentration of the material gives rise to an error in measured concentration in principle because of the presence of multiple materials produced by the decomposition.

On the other hand, in the past, the optical type concentration measuring device has measured the concentration of Cp$_2$Mg on the basis of absorbance around 3.4 μm that is within the light absorption band of Cp$_2$Mg. However, the light absorption band of the organic substance produced by the decomposition of Cp$_2$Mg is also present around 3.4 μm, and therefore due to the effect of the organic substance, an error occurs in Cp$_2$Mg measured concentration.

CITATION LIST

Patent Literature

Patent Literature 1: JP-A2006-324532

SUMMARY OF INVENTION

Technical Problem

The present invention is made in consideration of the above-described problem, and intends to provide a Cp$_2$Mg concentration measuring device capable of accurately measuring the concentration of Cp$_2$Mg to be supplied to a process chamber with little effect of spontaneous decomposition.

Solution to Problem

That is, the Cp$_2$Mg concentration measuring device according to the present invention is one that is attached to a supply pipe for supplying material gas containing Cp$_2$Mg to a process chamber, and adapted to include: a cell, which has mutually opposite first and second windows and into which the material gas flowing through the supply pipe is introduced; a light source unit adapted to irradiate the inside of the cell with light through the first window; and a light receiving unit adapted to receive light led out of the second window through the inside of the cell.

In addition, light transmissive members forming the respective windows are ones allowing light having wavelengths including the fingerprint region of Cp$_2$Mg (light having wavelengths including wavelengths around 12.8 μm) to transmit therethrough without substantially attenuating the light, i.e., to the extent of not affecting measurement, and the light receiving unit includes: a light intensity measuring part adapted to measure light intensity in a predetermined wavelength band around 12.8 μm; and a concentration calculation part adapted to, on the basis of the light intensity, calculate the concentration of Cp$_2$Mg in the material gas.

The fingerprint region refers to a wavelength region where an absorption peak caused by stretching vibration or bending vibration of the specific chemical structure of a measurement target appears, and also a region where an absorption pattern specific to each compound is exhibited. In the case of Cp$_2$Mg, in the fingerprint region around 12.8 μm, an absorption caused by bending vibration in which the bonding angle between carbon and hydrogen varies with respect to the carbon bond face of a cyclopentadienyl group is observed. Similarly, a compound having a Cp$_2$Mg skeleton absorbs light around 12.8 μm regardless of functional groups.

The specific light absorption band of Cp$_2$Mg is present around 12.8 μm, whereas an organic substance produced by the decomposition of Cp$_2$Mg has little light absorption in that wavelength band. Accordingly, the above-described configuration makes it possible to accurately measure the concentration of Cp$_2$Mg in the material gas to be supplied to the process chamber without being affected by the spontaneous decomposition of Cp$_2$Mg.

Next, the reason why in the past, the concentration of Cp$_2$Mg has not been measured on the basis of light intensity around 12.8 μm despite the presence of such an effect will be described.

A supply pipe to a process chamber requires extremely high airtightness. This is because even the occurrence of a small amount of leakage causes not only the instability of the supply amount of $Cp_2Mg$ but also a safety problem and the like.

However, various materials such as ZnSe used as a light transmissive member allowing light having wavelengths around 12.8 μm to transmit therethrough have the disadvantage of the difficulty of airtight attachment.

Meanwhile, as described above, in the past, it has been considered that $Cp_2Mg$ is stable and not decomposed, and in terms of accuracy, the measurement of absorbance around 3.4 μm is good enough. In addition, as a material allowing light around 3.4 μm to transmit therethrough, sapphire and the like having the ease of airtight attachment are present.

Accordingly, in the past, a person skilled in the art has never had the idea of as the light transmissive material, purposely using ZnSe or the like requiring time and effort to keep airtightness.

In that sense, the present invention is a remarkable one that has been made precisely because the present inventor has first found that even at low temperatures, $Cp_2Mg$ decomposes to the extent of affecting required measurement accuracy.

Specific embodiments capable of preferably keeping the airtightness of the windows include one in which the cell is one that includes: a cell main body that has a pair of openings and is made of metal; and window forming members that airtightly seal the openings and form the windows, respectively, and the window forming members are ones that include: metallic ring plates; and the light transmissive members airtightly crimped to the metallic ring plates through seal materials, respectively.

As a preferable embodiment of the seal materials, elastic metallic seal materials can be cited.

In the $Cp_2Mg$ concentration measuring device in which the cell main body for flowing the material gas to the cell is one that includes a tubular-shaped central member and flange members respectively integrally provided at both ends of the central members, and the cell is configured by airtightly attaching the window forming members to the flange members, respectively, as a preferable embodiment for circulating the material gas in the cell, it is preferably that a gas introduction path and a gas lead-out path are respectively provided in the flange members. Such a configuration makes it possible to make dead volume where the gas is likely to accumulate as small as possible in the internal space of the cell, and thereby surely replace or purge the gas in a short period of time.

It is more desirable that the light transmissive members forming the respective windows are ones also allowing light having wavelengths including wavelengths around 3.4 μm to transmit therethrough without substantially attenuating the light, and the light receiving unit further includes: a second light intensity measuring part adapted to measure light intensity in a predetermined wavelength band around 3.4 μm; a second concentration calculation part adapted to, on the basis of the light intensity, calculate the concentration of $Cp_2Mg$ in the material gas; and a third concentration calculation part adapted to, by comparing the $Cp_2Mg$ concentration calculated by the concentration calculation part and the $Cp_2Mg$ concentration calculated by the second concentration calculation part with each other, calculate the concentration of an organic substance or magnesium produced by the decomposition of $Cp_2Mg$. Deposited film quality can be improved by some means such as monitoring the organic substance concentration in the material gas and when the concentration exceeds a threshold value, stopping a process.

Advantageous Effects of Invention

According to the present invention, the concentration of $Cp_2Mg$ to be supplied to a process chamber can be measured with extreme accuracy even when the concentration is low.

DESCRIPTION OF EMBODIMENTS

Figure 1:
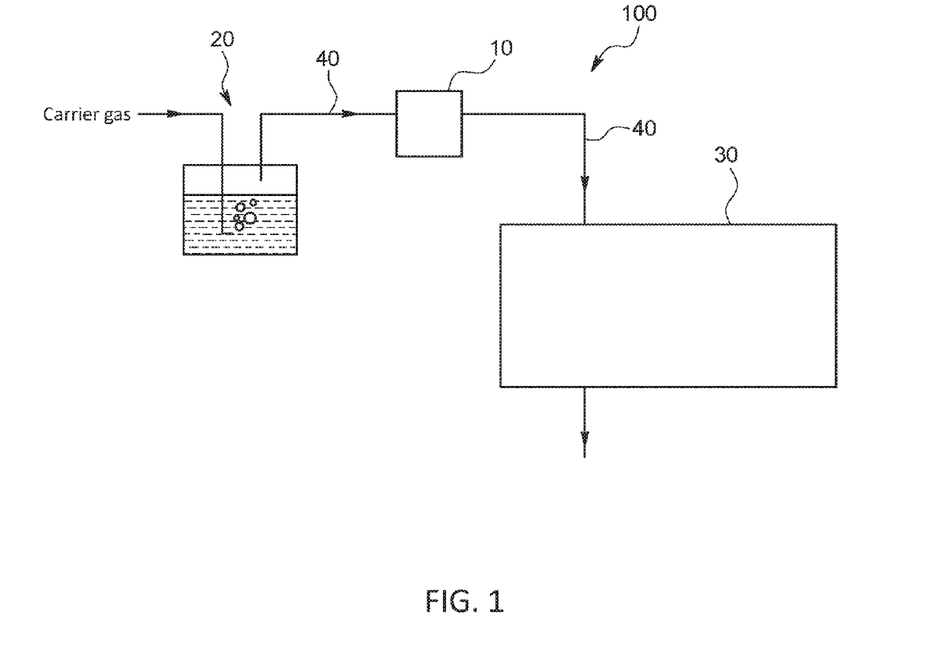
FIG. 1 is a schematic diagram of a semiconductor manufacturing system according to one embodiment of the present invention.

A $Cp_2Mg$ concentration measuring device 10 according to the present embodiment is one that, for example, constitutes part of a semiconductor manufacturing system 100. As illustrated in FIG. 1, the semiconductor manufacturing system 100 is one that includes at least a process chamber 30 in which a film is deposited in order to manufacture photoelectric conversion elements such as LEDs or solar cells, a material gas supply source 20 adapted to supply material gas for the film deposition, and a supply pipe 40 adapted to introduce the material gas from the material gas supply source 20 to the process chamber 30.

More specifically, the $Cp_2Mg$ concentration measuring device 10 will be described.

Figure 2:
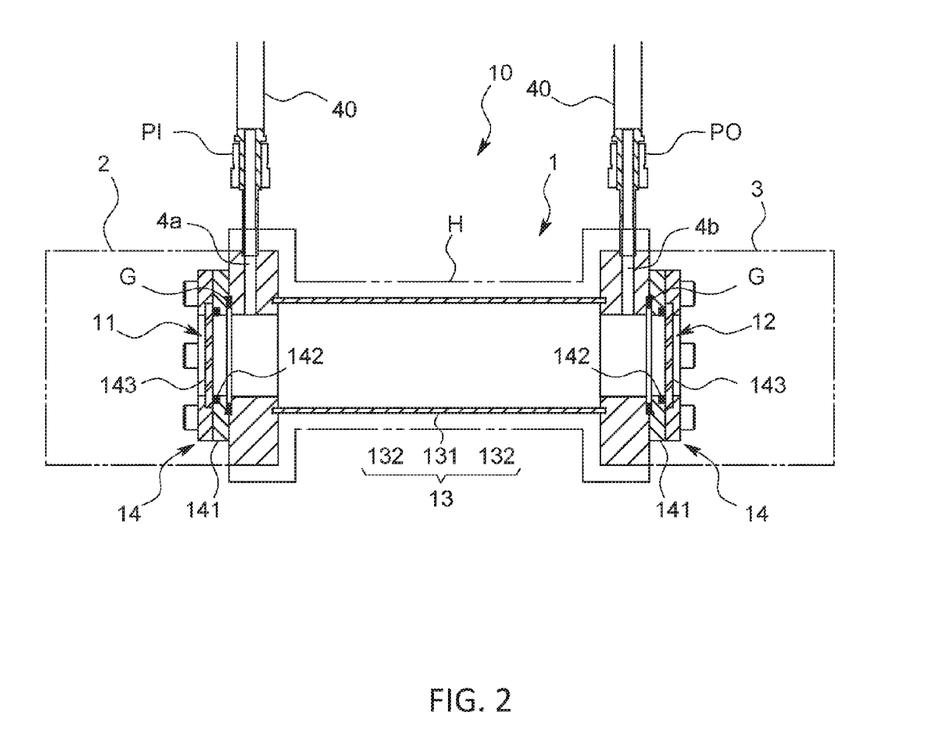
FIG. 2 is a vertical cross-sectional view illustrating a $Cp_2Mg$ concentration measuring device in the same embodiment.

The $Cp_2Mg$ concentration measuring device 10 is, for example, an NDIR type measuring device that as illustrated in FIG. 2, is attached to the supply pipe 40 to measure the concentration of $Cp_2Mg$ in the material gas flowing through the supply pipe 40, and includes: a cell 1 into which the material gas flowing through the supply pipe 40 is introduced; a light source unit 2 adapted to irradiate the inside of the cell 1 with light through a first window 11 provided for the cell 1; and a light receiving unit 3 adapted to receive light led out of a second window 12 provided for the cell 1.

Figure 3:
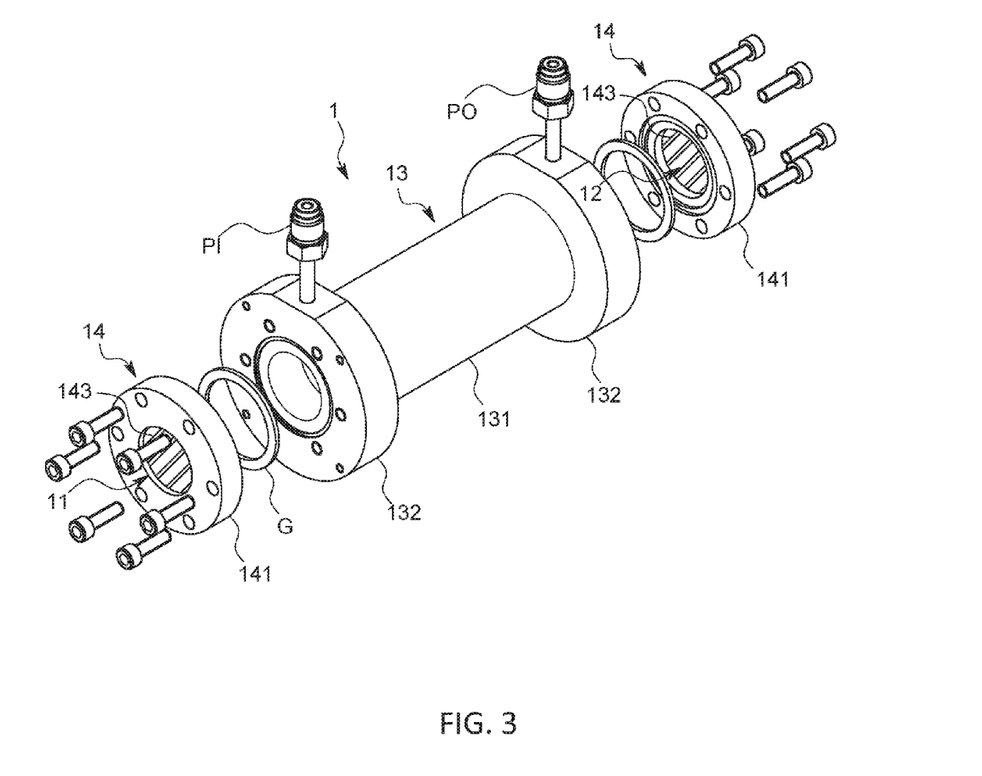
FIG. 3 is an exploded perspective view illustrating a cell of the $Cp_2Mg$ concentration measuring device in the same embodiment.

The cell 1 is one that as illustrated in FIGS. 2 and 3, includes a tubular-shaped cell main body 13 and window forming members 14 that airtightly close both end openings of the cell main body 13.

The cell main body 13 is a metallic one (specifically, made of SUS 316L) including a cylindrical-shaped central member 131 having a uniform diameter, and flange members 132 that are respectively integrally provided on both ends of the central member 131 and have a predetermined thickness. The inner circumferential surface of the cell main body is electrolytically polished in order to suppress gas adsorption.

The window forming members 14 are ones that respectively include: metallic ring plates 141 having diameters slightly smaller than those of the flange members 132; and disc-shaped ZnSe plates 143 as light transmissive members that are airtightly crimped to the metallic ring plates 141 through special elastic metallic seal materials 142 (specifically, made of aluminum).

Each of the ZnSe plates 143 is one that allows light having wavelengths at least in a band of 3.4 µm to 12.8 µm and also in a predetermined band around the band to pass therethrough substantially hardly attenuating the light.

By airtightly attaching the metallic ring plates 141 of the window forming members 14 to the flange members 132 through metallic gaskets G for sealing, the pair of mutually opposite windows 11 and 12 formed of the ZnSe plates 143 are formed, respectively and correspondingly.

The cell 1 is provided with: a gas introduction port PI that is connected to the material gas supply source 20 through the upstream side supply pipe 40; and a gas lead-out port PO that is connected to the process chamber 30 through the downstream side supply pipe 40. This configuration allows the total amount of the material gas outputted from the material gas supply source 20 to be supplied to the process chamber 30 through the internal space of the cell 1.

The gas introduction port PI and the gas lead-out port PO are attached to the outer circumferential surfaces of corresponding ones of the flange members 132. On the other hand, the flange members 132 extend in their radial direction, and include gas introduction and lead-out paths 4a and 4b that communicatively connect between the outer circumferential surfaces thereof and the internal space of the cell 1, respectively and correspondingly. Also, the outer opening parts of the gas introduction and lead-out paths 4a and 4b are respectively attached with the gas introduction port PI and the gas lead-out port PO.

In addition, as illustrated in FIG. 2, the cell 1 is covered with a heater H entirely, except for both end surfaces formed with the windows 11 and 12. In doing so, the cell 1 is heated to a temperature (30° C. to 50° C.) enough to prevent the thermal decomposition and condensation of $Cp_2Mg$ flowing inside.

Figure 4:
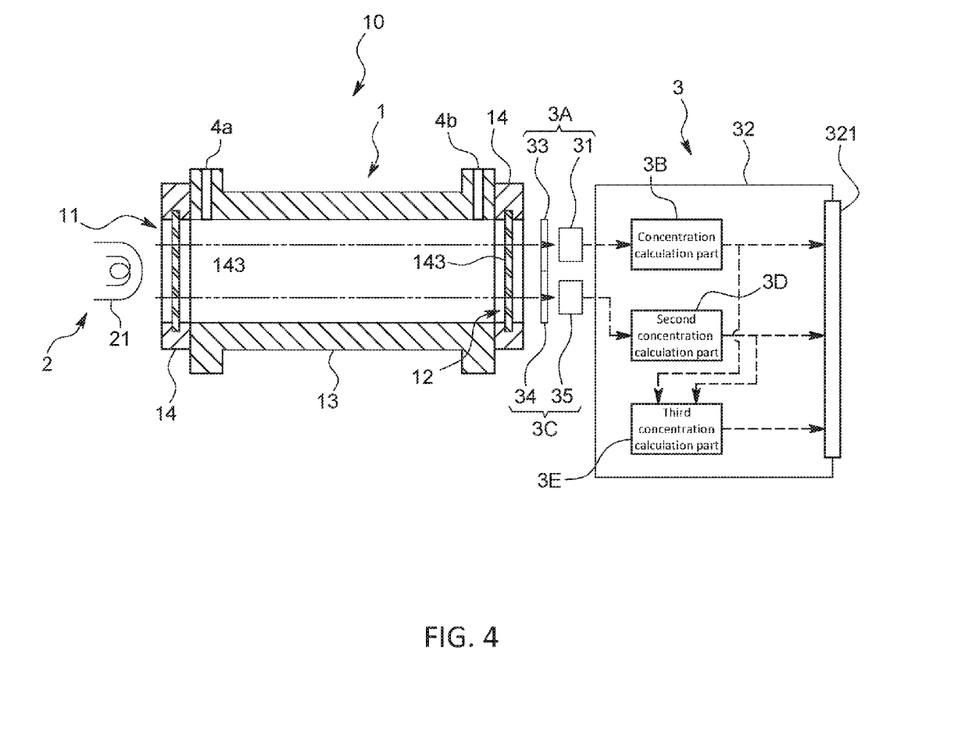
FIG. 4 is a schematic diagram illustrating the functions of the $Cp_2Mg$ concentration measuring device in the same embodiment.

The light source unit 2 is one that as schematically illustrated in FIG. 4, includes a light source 21 provided so as to face to the first window 11. The light source 21 is, for example, a filament type light source adapted to emit wideband infrared light, and configured such that the light emitted from the light source 21 passes through the first window 11, irradiates the internal space of the cell 1 in which the material gas flows, and exits from the second window 12.

The light receiving unit 3 is one that as schematically illustrated in FIG. 4, includes: a light receiving element 31 provided so as to face to the second window 12; a wavelength selection filter 33 that is arranged between the light receiving element 31 and the second window 12, and filters the light exiting from the second window 12 such that only light having some wavelengths enters the light receiving element 31; and an information processing circuit 32 that calculates the concentration of $Cp_2Mg$ in the material gas, or the like, on the basis of light intensity outputted by the light receiving element 31.

The wavelength selection filter 33 and the light receiving element 31 function as a light intensity measuring part 3A adapted to measure the intensity of light in a predetermined band around a wavelength of 12.8 µm.

The information processing circuit 32 is one including, for example, a digital circuit having a CPU, memory, communication circuit, and the like; and an analog circuit having an amplifier, AD converter and the like, all of which are not illustrated. Also, the CPU and its peripheral circuits cooperate in accordance with a program preliminarily stored in the memory, and thereby, as illustrated in FIG. 4, the information processing circuit 32 functions as a concentration calculation part 3B adapted to calculate the concentration (herein after also referred to as a first concentration) of $Cp_2Mg$ in the material gas from the light intensity measured by the light receiving element 31.

Figure 5:
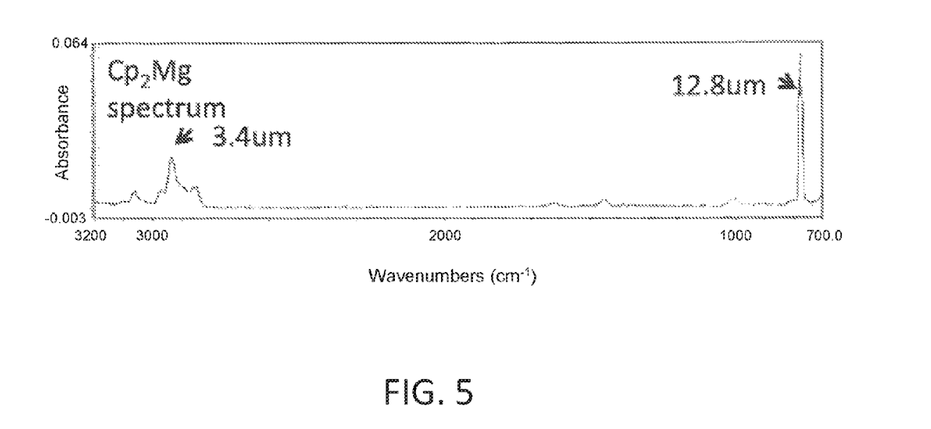
FIG. 5 is an absorption spectrum diagram illustrating the absorption characteristics of $Cp_2Mg$.

The principle of the concentration calculation will be briefly described. As illustrated in FIG. 5, it turns out that the light absorption spectrum of $Cp_2Mg$ has a strong peak around a wavelength of 12.8 µm, and therefore $Cp_2Mg$ absorbs light in a band around the wavelength. Accordingly, by measuring light intensity in the band to obtain absorbance, the partial pressure of $Cp_2Mg$ in the material gas can be obtained on the basis of the absorbance and a calibration curve that was preliminarily prepared and recorded in the memory.

Once the partial pressure of $Cp_2Mg$ in the material gas is obtained, the concentration of $Cp_2Mg$ can be calculated on the basis of the partial pressure of $Cp_2Mg$ and the total pressure of the material gas inside the cell measured by an unillustrated pressure gauge provided in the cell or in the pipe before or after the cell.

Further, the first concentration calculated as described is outputted as the $Cp_2Mg$ concentration from an external output port 321 provided in the information processing circuit 32. The semiconductor manufacturing system 100 controls the supply amount of $Cp_2Mg$ to be mixed with the carrier gas with the first concentration as a target value.

Meanwhile, as illustrated in FIG. 5, the light absorption spectrum of $Cp_2Mg$ also has a peak around a wavelength of 3.4 µm, and therefore $Cp_2Mg$ also absorbs light in a band around the wavelength.

Therefore, the present embodiment is adapted to calculate the concentration of $Cp_2Mg$ from absorbance in the band around the wavelength of 3.4 µm.

Specifically, as illustrated in FIG. 4, a second light intensity measuring part 3C adapted to receive light in a predetermined band around the wavelength of 3.4 µm among the light exiting from the second window 12, and output the intensity of the received light is provided in the light receiving unit 3.

The second light intensity measuring part 3C is one including: a second light receiving element 35 arranged so as to face to the second window 12, and a second wavelength selection filter 34 arranged between the second light receiving element 35 and the second window 12.

Also, a second concentration calculation part 3D adapted to calculate the concentration (hereinafter also referred to as a second concentration) of $Cp_2Mg$ from the light intensity measured by the second light intensity measuring part 3C is provided in the information processing circuit 32.

The present inventor has found that as described above, $Cp_2Mg$ spontaneously decomposes into magnesium and the organic substance (methane) even at low temperatures lower than the thermal decomposition temperature. The organic substance produced by the decomposition has a light absorption band around the wavelength of 3.4 µm, and therefore the second concentration includes an error due to the light absorption by the organic substance.

The present embodiment takes advantage of this to further provide a third concentration calculation part 3E adapted to, by comparing the first concentration including little error as the $Cp_2Mg$ concentration and the second concentration including the error caused by the organic substance with each other, calculate the concentration of the organic substance or the concentration of decomposed $Cp_2Mg$ from, for example, the difference between the first and second concentrations. The concentration of the organic substance is outputted from the external output port 321 provided in the information processing circuit 32.

Note that the light intensity outputted by each of the light receiving elements 31 and 35 also depends on the light intensity of the light source 21, and therefore it is necessary to measure the light intensity of the light source 21 as a reference to normalize the value of the light intensity outputted by that light receiving element 31 or 35 using the reference. For this purpose, the present embodiment is adapted to provide a reference light receiving element (not illustrated) in the light receiving unit 3, selectively guide light in a wavelength band where the material gas does not absorb any light to the reference light receiving element through a filter, and use the value of the output signal of the reference light receiving element as the reference.

The $Cp_2Mg$ concentration measuring device 10 configured as described can have the following effects.

Since the concentration of $Cp_2Mg$ in the material gas is measured using the light intensity around 12.8 μm where the organic substance produced by the decomposition of $Cp_2Mg$ does not absorb any light, extremely high measurement accuracy can be obtained.

Since the gas introduction path 4a and the gas lead-out path 4b are provided in the flange members 132 constituting both end parts of the cell 1, respectively and correspondingly, and in the internal space of the cell 1, dead volume where the gas is likely to accumulate is reduced as much as possible, it is possible to surely replace or purge the gas in a short period of time.

The present inventor has found that the concentration of the organic substance produced by the decomposition of $Cp_2Mg$ tends to be high at the start of supplying $Cp_2Mg$ and then decrease. As the reason for this, the present inventor considers that since $Cp_2Mg$ spontaneously decomposes during storage, and the organic substance produced by the decomposition is first discharged (because of its low specific gravity), after a certain amount of time has passed since the start of the supply, the concentration is low. Since in response to this phenomenon, the $Cp_2Mg$ concentration measuring device 10 of the present embodiment is adapted to also measure and output the concentration of the organic substance, for example, after the concentration of the organic substance has become a predetermined threshold value or less, it is possible to start the film deposition, or when the concentration of the organic substance exceeds the threshold value for some unexpected reason, it is possible to stop the film deposition, and therefore the quality of the deposited film can be improved.

Since the cell 1 is kept by the heater H at a temperature enough to substantially prevent the thermal decomposition and condensation of $Cp_2Mg$, $Cp_2Mg$ is not lost inside the cell 1. Accordingly, the supply amount of $Cp_2Mg$ to the process chamber 30 can be stabilized.

The ZnSe plates 143 used as the light transmissive members can have extremely high sealing performance for some reasons such as having no deliquescency, high hardness, and small expansion coefficient. In addition, the ZnSe plates 143 are high in thermal conductivity as well, and therefore surely heated by the heater H to prevent the windows from being easily fogged due to condensation or the like. Further, the ZnSe plates 143 also have the advantage of high heat resistance temperature.

The ZnSe plates 143 are made dirty or fogged by being used, and therefore it is necessary to replace them at the time of maintenance or the like. When doing the maintenance, the ZnSe plates 143 can be replaced integrally as the window forming members 14, respectively and correspondingly, and therefore as compared with replacing only the ZnSe plates 143, work is easy and airtightness is easily secured.

Note that the present invention is not limited to the above-described embodiment.

For example, the concentration of $Cp_2Mg$ may be measured using not the NDIR but a spectroscopic analyzer such as an FTIR. The $Cp_2Mg$ concentration measuring device according to the present invention can also be applied when manufacturing not only the photoelectric conversion elements but also different types of semiconductor elements.

Also, the windows 11 and 12 are not necessarily required to face to each other, but may be configured not to face to each other by inserting a mirror inside the cell 1.

It may be configured that the concentration calculation part, second concentration calculation part, or third concentration calculation part is one that calculates the concentration of $Cp_2Mg$ or the like in the material gas or a basic value for calculating the concentration, and the concentration or the basis value is outputted from the external output port provided in the information processing circuit.

The basic value refers to, for example, the absorbance or the partial pressure of $Cp_2Mg$ or the like in the material gas.

More specifically, it may be configured that the concentration calculation part or the second concentration calculation part is one adapted to calculate the absorbance of the material gas on the basis of the light intensity measured by a corresponding one of the light intensity measuring parts, or one adapted to calculate the partial pressure of $Cp_2Mg$ in the material gas on the basis of the absorbance and the preliminarily prepared calibration curve recorded in the memory, and the third concentration calculation part is one adapted to calculate the absorbance or partial pressure of the organic substance or magnesium produced by the decomposition of $Cp_2Mg$ by comparing the absorbances or partial pressures calculated by the concentration calculation part and the second concentration calculation part.

Besides, various modifications and combinations of the embodiments may be made without departing from the scope of the present invention.

REFERENCE SIGNS LIST

30: Process chamber
40: Supply pipe
10: $Cp_2Mg$ concentration measuring device
1: Cell
11: First window
12: Second window
13: Cell main body
131: Central member
132: Flange member
14: Window forming member
142: Seal material (elastic metallic seal material)
143: Light transmissive member (ZnSe plate)
2: Light source unit
3: Light receiving unit
3A: Light intensity measuring part
3B: Concentration calculation part
3C: Second light intensity measuring part
3D: Second concentration calculation part
3E: Third concentration calculation part
4a: Gas introduction path
4b: Gas lead-out path

The invention claimed is:

1. A $Cp_2Mg$ concentration measuring device that is attached to a supply pipe for supplying material gas containing Cp$_2$Mg to a process chamber, the Cp$_2$Mg concentration measuring device comprising:

a cell into which the material gas flowing through the supply pipe is introduced, the cell having a first window and a second window; a light source unit adapted to irradiate an inside of the cell with light through the first window; and a light receiving unit adapted to receive light led out of the second window through the inside of the cell, wherein light transmissive members forming the respective windows are ones allowing light having wavelengths including wavelengths around 12.8 μm to transmit therethrough, and the light receiving unit comprises: a light intensity measuring part adapted to measure light intensity in a predetermined wavelength band around 12.8 μm; and a concentration calculation part adapted to, on a basis of the light intensity, calculate a concentration of Cp$_2$Mg in the material gas or a basic value for calculating the concentration of Cp$_2$Mg.

2. The Cp$_2$Mg concentration measuring device according to claim 1, wherein a material of the light transmissive members is ZnSe.

3. The Cp$_2$Mg concentration measuring device according to claim 1, wherein the cell is one that comprises: a cell main body that has a pair of openings and is made of metal; and window forming members that airtightly seal the openings and form the windows, respectively, and the window forming members are ones that comprise: metallic ring plates; and the light transmissive members airtightly crimped to the metallic ring plates through seal materials, respectively.

4. The Cp$_2$Mg concentration measuring device according to claim 3, wherein the seal materials are elastic metallic seal materials, respectively.

5. The Cp$_2$Mg concentration measuring device according to claim 3, wherein:

the cell main body is one that comprises a tubular-shaped central member and flange members integrally provided at both ends of the central members, and the cell is one in which the window forming members are airtightly attached to the flange members, respectively and correspondingly; and a gas introduction path and a gas lead-out path for circulating the material gas in the cell are respectively provided in the flange members, respectively and correspondingly.

6. The Cp$_2$Mg concentration measuring device according to claim 1, wherein the light transmissive members forming the respective windows are ones also allowing light having wavelengths including wavelengths around 3.4 μm to transmit therethrough, and the light receiving unit further comprises:

a second light intensity measuring part adapted to measure light intensity in a predetermined wavelength band around 3.4 μm;

a second concentration calculation part adapted to, on a basis of the light intensity, calculate a concentration of Cp$_2$Mg in the material gas or a basic value for calculating the concentration of Cp$_2$Mg; and a third concentration calculation part adapted to, by comparing the Cp$_2$Mg concentration calculated by the concentration calculation part and the Cp$_2$Mg concentration calculated by the second concentration calculation part with each other, or the basic value calculated by the concentration calculation part to calculate the Cp$_2$Mg concentration and the basic value calculated by the second concentration calculation part to calculate the Cp$_2$Mg concentration with each other, calculate a concentration of an organic substance or magnesium produced by decomposition of Cp$_2$Mg, or a basic value for calculating the concentration of an organic substance or magnesium.

\* \* \* \* \*